United States Patent
Hamer et al.

(10) Patent No.: US 6,167,745 B1
(45) Date of Patent: *Jan. 2, 2001

(54) TESTING APPARATUS

(75) Inventors: Clive Hamer; John Hutchinson, both of London (GB)

(73) Assignee: PCS Limited, London (GB)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/137,113

(22) Filed: Aug. 20, 1998

(30) Foreign Application Priority Data

Aug. 23, 1997 (GB) .................................... 9717840

(51) Int. Cl.$^7$ ...................................... G01N 3/56
(52) U.S. Cl. ................................................. 73/9
(58) Field of Search ................................. 73/9, 10

(56) References Cited

U.S. PATENT DOCUMENTS 4,023,402 * 5/1977 Watanabe .
5,115,664 * 5/1992 Hegde et al. .............................. 73/9
5,377,525 * 1/1995 Hutchinson et al. .................... 73/10
5,679,883 * 10/1997 Wedeven .................................. 73/10

FOREIGN PATENT DOCUMENTS 1105319   3/1968 (GB) .
WO 94/05449  3/1994 (WO) .

* cited by examiner

Primary Examiner—Robert Raevis
(74) Attorney, Agent, or Firm—Oliff & Berridge, PLC

(57) ABSTRACT

Traction and/or friction testing apparatus is described having inter-engaging, rotating, traction surfaces, the surfaces being independently driven to generate traction or friction forces therebetween. A force measuring means is provided to measure the resulting traction or friction force. The apparatus is characterised in that all forces applying in the traction measurement loop are directly readable, or elastic, thus eliminating internal friction and allowing an accurate indication of the traction or friction force. The apparatus is particularly useful for measuring rolling/sliding traction and friction.

12 Claims, 5 Drawing Sheets

TESTING APPARATUS

TECHNICAL FIELD

This invention relates to testing apparatus and, in particular, to apparatus for testing rolling traction and/or friction forces. Typical applications include fuel economy modelling of automotive engine oils, boundary additive evaluation and friction measurements for traction fluids.

BACKGROUND OF THE INVENTION

A number of forms of apparatus have been proposed, in the past, for testing friction and/or traction forces. However, accurate measurement is difficult to achieve as known forms of testing apparatus have in-built resistances, such as internal friction, which can influence the total force the apparatus is attempting to measure.

By way of example, traction in rolling/sliding contacts is usually determined by measuring torque applied to one of the rotating specimens or by measuring the reaction force felt by a body supporting one of the rotating specimens.

If measuring the torque applied, it is normally necessary to position the torque transducer behind bearings supporting the specimen drive shaft. This means that the transducer is also measuring the torque applied to overcome frictional resistance in the bearings and/or oil seal and is thus not giving an accurate measurement of the applied torque alone.

If measuring the reaction force, this is normally measured by a force transducer which constrains the body supporting one of the rotating specimens from moving in the direction of the traction force. Because of the applied load, the body is, normally, supported by additional means. In order to maximise the accuracy of the traction measurement, the additional means of support needs to have extremely low resistance to motion in the direction of the traction force. This is typically achieved by using rolling element bearings or air bearings within the additional support. However, whilst such bearings have very low frictional resistance, they have sufficient resistance to reduce the accuracy of the traction measurement. Also, such frictional resistance as they do have will normally vary with variations in magnitude of the applied load.

For practical purposes it may not be possible to entirely eliminate extraneous forces. What is therefore required is a form of apparatus in which any extraneous forces are predictable and which can thus be eliminated by a calibration process.

It is an object of this invention to provide traction and/or friction testing apparatus in which any extraneous force inherent in the apparatus is predictable such that any measurement of traction or friction force will be directly proportional to the actual force.

SUMMARY OF THE INVENTION

Accordingly, in one aspect, the invention comprises traction or friction testing apparatus, said apparatus comprising:

a first traction surface;

a second traction surface constructed and arranged to, in use, contact said first traction surface, said first and second traction surfaces being arranged for rotational engagement therebetween;

a support structure constructed and arranged to support said first and second traction surfaces with respect to one another whilst allowing rotational movement therebetween;

drive means operable to effect differential rotation between said first and second traction surfaces and thereby to generate a traction or friction force therebetween; and force measuring means associated with at least said first and second traction surfaces to provide a measure arising from said traction or friction force, said apparatus being characterised in that any force arising between said first and said second traction surfaces due to traction or friction therebetween is resisted solely by elastic deformation of said support structure and/or said force measuring means.

The subject invention is constructed and arranged to measure rolling traction and/or friction. To that end, the first traction surface is conveniently planar in form whilst the second traction surface has a circular component to allow rotating motion thereof with respect to the first surface. More preferably, the second traction surface is provided by the surface of a spherical ball.

In a particularly preferred form, the first traction surface comprises a planar disc adapted to be mounted for rotation about its central axis.

The support structure preferably includes first support means constructed and arranged to rotatably mount said first traction surface; and second support means constructed and arranged to rotatably support said second traction surface, said first and second support means being relatively displaceable to allow said first and second traction surfaces to be moved into contact with their respective axes of rotation lying in a substantially common plane.

Conveniently, the first support means mounts said first traction surface for rotation about a substantially vertical axis. The second support means is mounted for pivotal movement about a substantially horizontal axis to permit said second traction surface to be displaced into contact with said first traction surface.

Preferably said second support means further includes elastic flexure means constructed and arranged to permit elastic movement of said second traction surface with respect to said first traction surface in the direction of the resulting traction or friction force, yet resist movement of said second traction surface in orthogonal directions.

The drive means may include a first drive motor to rotate said first traction surface; and a second drive motor to rotate said second traction surface. The drive means may further include displacement means to variably displace said second traction surface into contact with said first traction surface in a direction normal to said first traction surface. This displacement means is conveniently provided, in part, by a stepper motor.

The force measuring means preferably comprises a linear force transducer mounted to detect movement of said second traction surface due to a traction or friction force being generated between said first and second traction surfaces.

Many variations in the way the invention may be performed will present themselves to those skilled in the art. The only limitations on the scope of the invention should be imposed by the appended claims and not by the description of one preferred embodiment which follows.

BRIEF DESCRIPTION OF THE DRAWINGS

One embodiment of the invention will now be described with reference to the accompanying drawings in which.

DESCRIPTION OF PREFERRED EMBODIMENT

Before commencing with a description of the apparatus and its operation, it is useful to define a few terms:

Slide/roll ratio is intended to mean the difference between the 2 speeds of the traction surfaces divided by their average. In other words $$\frac{2(V_1 - V_2)}{V_1 + V_2}$$

Rolling speed is the average of the speeds of first and second traction surfaces, i.e.

$$\frac{V_1 + V_2}{2}$$

Figure 1:
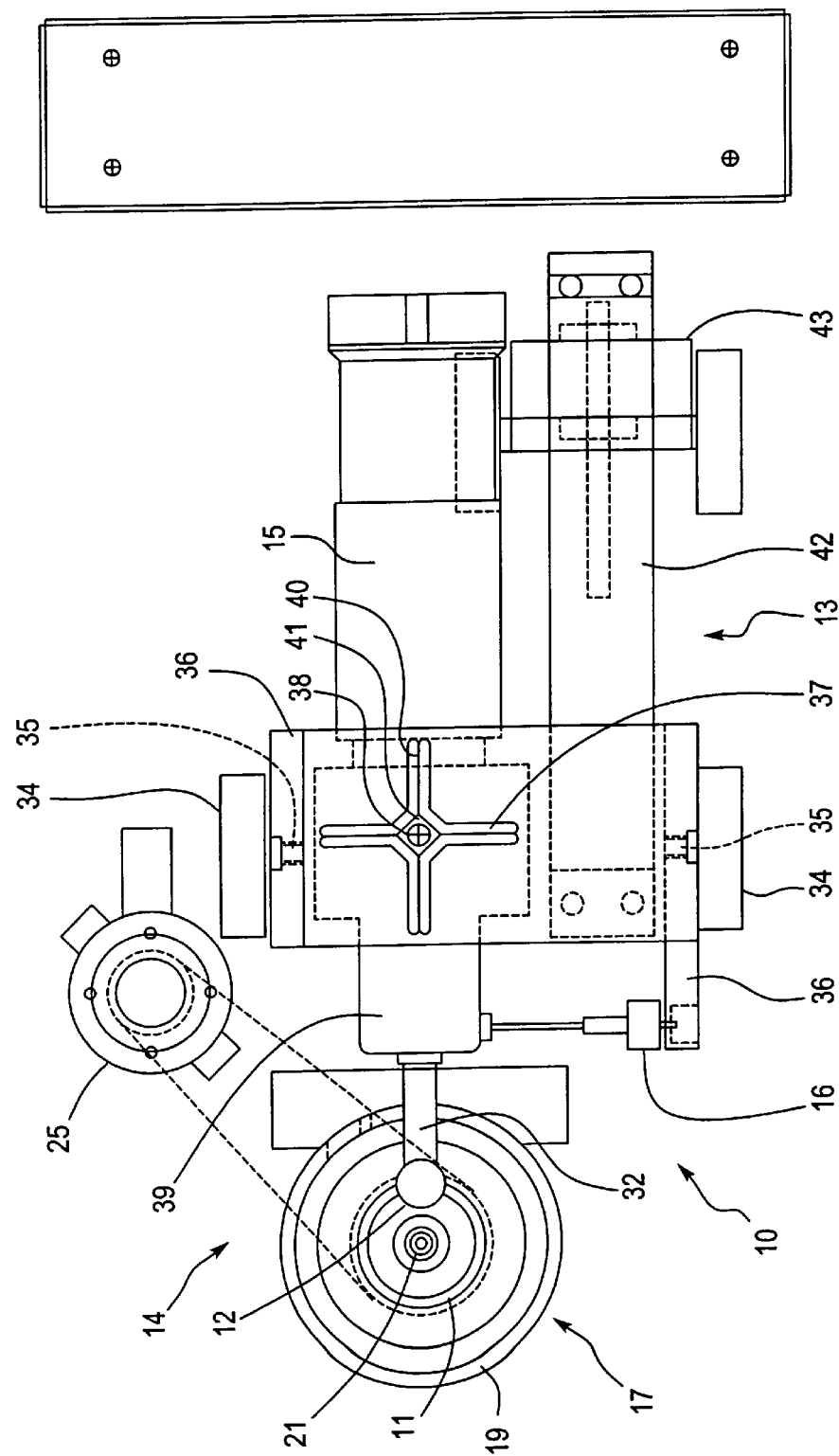
FIG. 1: shows a schematic plan view of testing apparatus embodying the invention.
Figure 2:
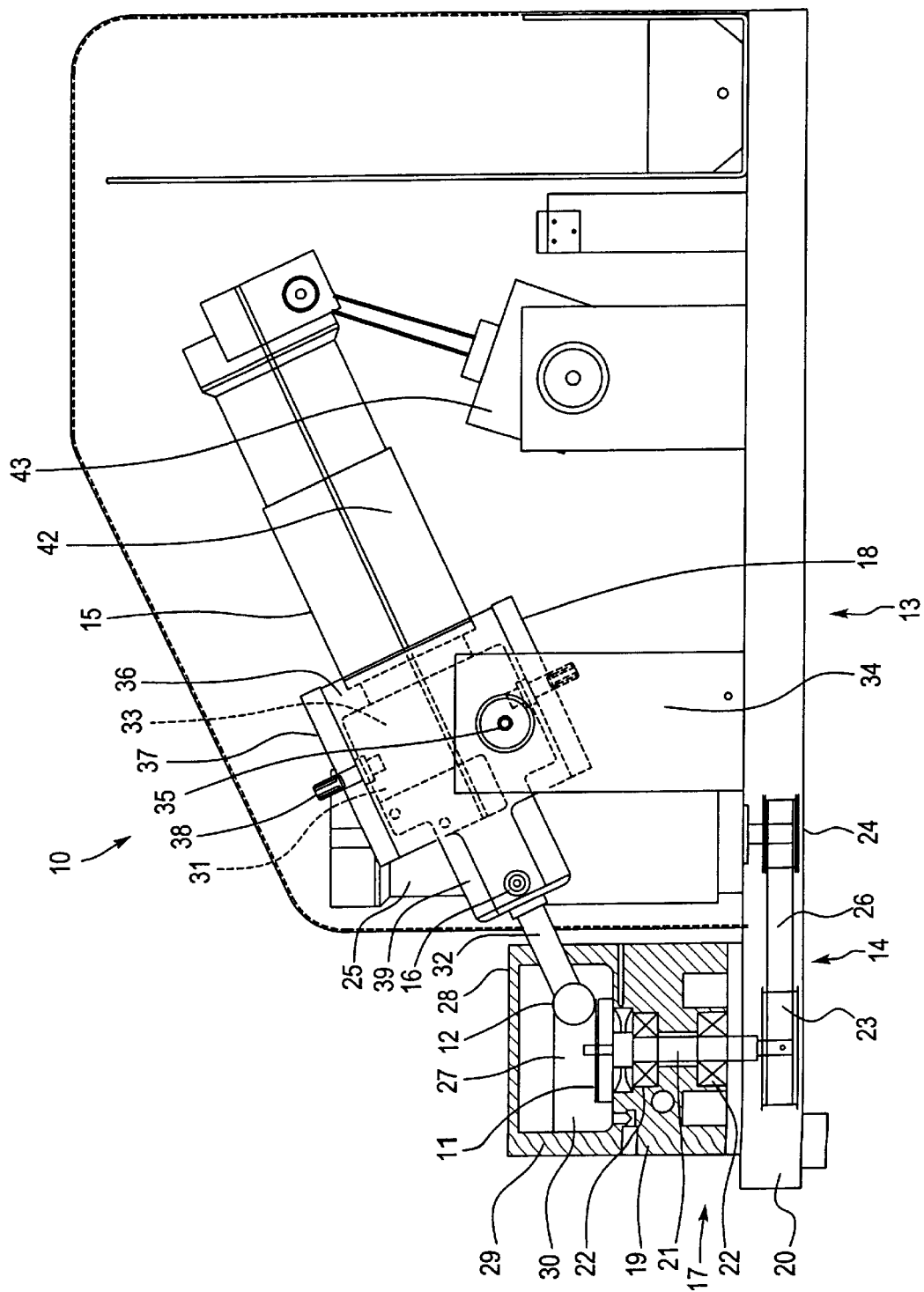
FIG. 2: shows a schematic side view, partly in section, of the testing apparatus shown in FIG. 1.
Figure 3:
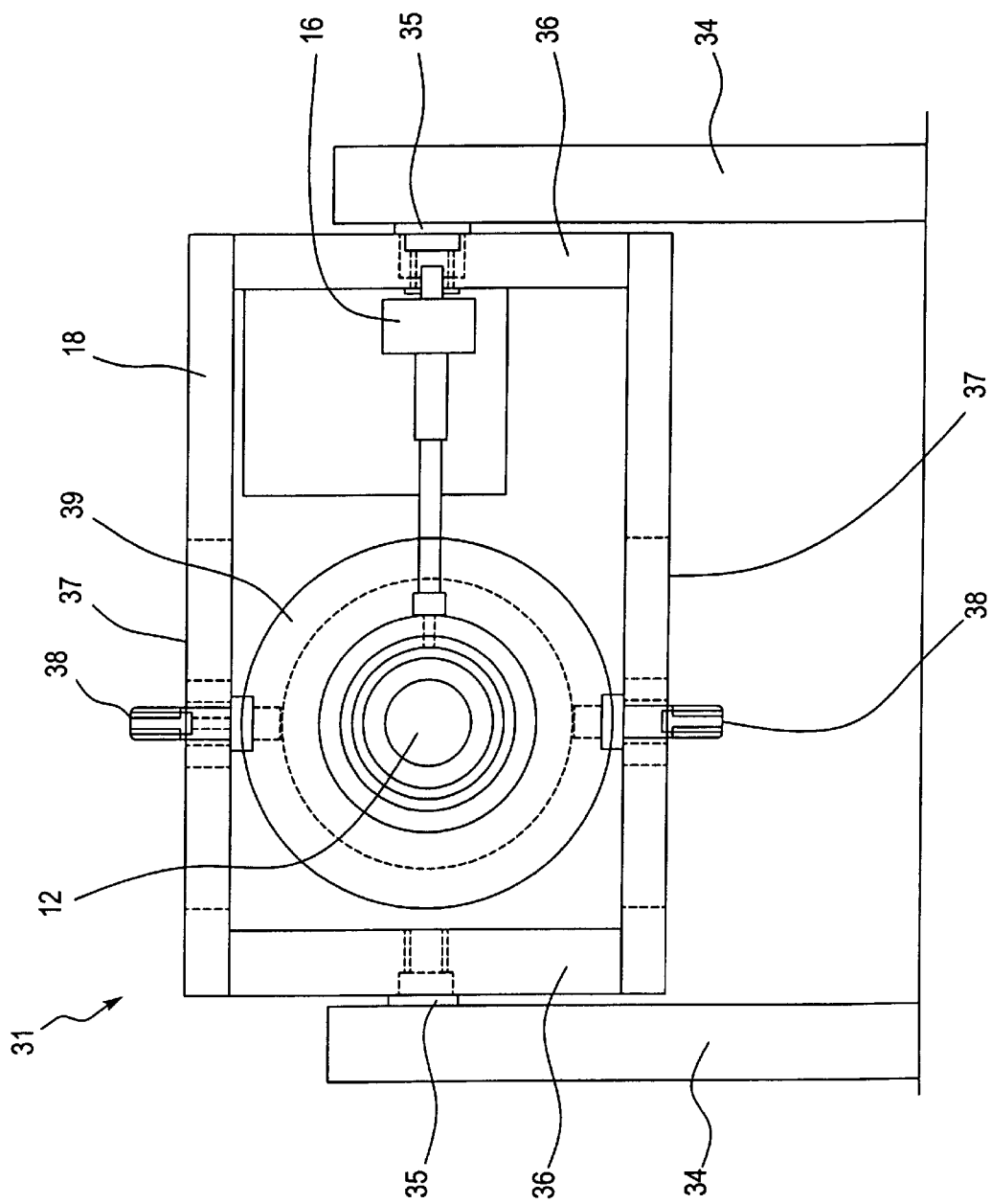
FIG. 3: shows (in a larger scale) a schematic end view, from the left as shown in FIGS. 1 & 2, of part of the testing apparatus shown in FIGS. 1 & 2 with the second traction surface in a raised position.

Turning to FIGS. 1 to 3, testing apparatus 10 is provided having a first traction surface 11 and a second traction surface 12, the surfaces 11 and 12 being arranged to contact one another as can be seen in FIGS. 1 & 2. A support structure, generally designated 13, is provided to support the surfaces 11 and 12 in their respective operating positions whilst allowing a certain amount of relative movement therebetween.

Mounted within the support structure 13 are drive means 14, 15 which are operable to effect respective movement of the traction surfaces 11 and 12 and, thereby, to generate a friction or traction force therebetween which, in use, is measured by force measuring means 16.

The apparatus 10 is characterised in that any traction or friction forces arising between the traction surfaces 11 and 12 are resisted solely by elastic deformation of the support structure and/or elastic deformation of the force measuring means 16.

In the form shown, the traction surfaces 11 and 12 are respectively configured to allow rolling movement with respect to one another. To this end, the first traction surface 11 is preferably a planar surface whilst the second surface 12 has a circular component such that, when the surface 12 is brought into contact with surface 11, rolling traction or friction forces can be generated. More advantageously, the planar first traction surface 11 is provided in the form of a disc mounted for rotation about its central axis by first drive means 14.

The second traction surface 12 is advantageously provided as the surface of a spherical ball mounted for rotation by second drive means 15. In one particular operating embodiment, the disc 11 is 46.0 mm in diameter and ball, 12, 19.05 mm in diameter. Both are formed from polished AISI 52100 bearing steel. They can, of course, be formed from other materials if desired. Both components are designed to be single use items, after which they are disposed of The support structure 13 includes first support means 17 to rotatably support the disc 11, and second support means 18 to rotatably support the ball 12, the first support means 12 and second support means 18 being so arranged with respect to each other that the axis of rotation of the ball 12 passes through the axis of rotation of the disc, the intersection of axes coinciding with the centre of the planar contact face of the disc 11. Thus, under pure rolling motion, contacting surface points in the contact patch will have substantially the same speed, so minimising a phenomenon known as spin in the contact. The shape of the contact is circular and is known as a Hertz contact.

More particularly, the first support means comprises bearing block 19 mounted on base chassis 20, the bearing block 19 mounting first drive shaft 21, in bearings 22, in a substantially vertical orientation. Disc 11 mounts on the upper end of the drive shaft 21, whilst mounted on the lower end of the shaft 21 is a drive pulley 23. Drive pulley 23 receives drive from a further pulley 24 mounted on the output shaft of DC servo motor 25, via drive belt 26.

Formed in the upper part of bearing block 19 is a fluid tight reservoir 27, the reservoir 27 being configured to retain a liquid under test, in a manner such that the contact patch between the disc 11 and ball 12, is immersed in the test fluid. The reservoir 27 is closed by a lid 28 along interface 29 which, as can be seen, is positioned above the contact patch between disc 11 and ball 12.

Electrical heating elements (not shown), or equivalents, are provided to heat the con tents of the reservoir 27, the temperature preferably being measured by platinum RTD type temperature probes 30. An external refrigerated oil cooler (not shown), or equivalent, may be provided to cool the contents of the reservoir 27.

The upper part of bearing block 19 and the lid 28, which in combination define the reservoir 27, are preferably clad in a PTFE insulating jacket to render the apparatus safe to touch even at the highest test temperatures.

The support structure 13 further includes second support means 31 which supports second drive means 15. The drive means 15 preferably comprises a further DC servo motor, ball 12 being mounted directly on output shaft 32 of the motor 15 for rotation thereby. The second support means 31 is arranged with respect to the first support means 17 so that the axes of disc 11 and ball 12 lie in a common vertical plane as can be seen in FIG. 1.

The use of independently driven DC servo motors as the drive motors 25 and 15 allows high precision speed control, particularly at low slide/roll ratios.

When in the testing configuration shown in FIGS. 1 & 2, with the ball 12 in contact with the disc 11, the output shaft 32 must pass through the wall which defines reservoir 27. This is advantageously accommodated by ensuring interface 29 is substantially coincident with the as o f shaft 32 when the ball 12 is in the loaded position as shown in FIG. 1. The lid 28 and bearing block 19, are provided, adjacent the interface 29, with co-operating semi-circular cavities (not shown) which, when the lid 28 is place in position over the upper part of bearing block 19 to define the reservoir 27, provide a clearance aperture about the shaft 32. Because interface 29 is above the working liquid level in the reservoir 27, shaft 32 does not need to be sealed where it passes through the reservoir wall. Obviously, if a shaft seal were used, such a seal would apply a resistive torque and reaction force to the shaft 32.

Motor 15 is mounted in a gimbal arrangement 33 mounted, in turn, in brackets 34 extending vertically from base chassis 20. Gimbal 33 is mounted to brackets 34 through stub shafts 35 mounted on a common horizontal axis. This allows the gimbal arrangement 33 to pivot about the horizontal axis and thereby bring the ball 12 into and out of contact with the disc 11. Further, by applying a loading force on the gimbal arrangement 33, about the horizontal axis of shafts 35 the force of ball 12 against disc 11 can be varied without varying any static interactive forces between the two, in orthogonal directions.

Stub shafts 35 project from rigid vertical side plates 36 which form part of the gimbal arrangement 33. Mounted between the upper and lower edges of the side plates 33 are flexures 37. Centrally located within each of the flexures 37, along a common axis orthogonal to the axis of stub shafts 35, are further stub shafts 38. The stub shafts 38 form part of mounting 39 in which motor 15 is mounted.

Each of the flexures 37 is configured and arranged to provide low torsional stiffness about the axis of stub shafts 38 yet provide high stiffness around any other rotational axis or in any translational direction. More importantly, the flexures 37 are configured and arranged to ensure that any resistance to movement, particularly about the axis of stub shafts 38, is purely elastic. In the embodiment depicted, the flexures 37 comprise four beams 40 which are arranged at right angles and which are relatively thin when viewed vertically as in FIG. 1. Whilst four beams 40 are depicted and described, it will be appreciated, by those skilled in the art, that three, or more than four, beams could be made to function equally effectively.

The beams 40 are preferably machined from aluminium and include a central hub 41 in which stub shafts 38 mount in a non-rotating manner. Thus, any rotation of the motor 15 about the axis of stub shafts 38 is resisted by elastic deformation of the flexure beams 40.

Projecting from the gimbal arrangement 33 is a loading beam 42, the outer end of which is linked to stepper motor 43 and a ball screw actuator to apply a displacement to the beam 42 and thereby displace the ball into and out of contact with disc 11 in a direction normal to the plane of disc 11. Once the ball has made contact with the disc, the actuator will cause the load beam 42 to bend and so, progressively increase the load applied to the disc. After calibration, the magnitude of the load can be precisely measured from the step count on the stepper motor or through strain gauges mounted on the load beam.

Finally, the force measuring means 16 is advantageously mounted on one of the vertical, rigid side plates 36 so as to contact mounting 39, supported in the flexures 37, which moves with the motor 15 and ball 12. Clearly, in this configuration, the force measuring means 16 resists movement of the mounting 39 about the axis of stub shafts 38.

The means 16 comprises a linear force transducer which is very much stiffer than the flexures 37 to maximise the sensitivity of the traction/friction measurement. However, the transducer 16 is also configured to ensure that any displacement thereof is elastic. Accordingly, it will be appreciated that because the transducer 16 and the flexures 37 form a linear elastic system, the transducer signal is directly proportional to any traction or friction force which arises between ball 12 and disc 11, and so can be calibrated to precisely measure the traction or friction force.

In use, before testing is commenced, the reservoir 27 is carefully cleaned and dried. Among suitable solvents for cleaning the reservoir are white spirits or varsol followed by iso-octane or heptane. In general, the first solvent should be chosen to give good removal of the types of lubricant under investigation, whilst the second solvent should be chosen to give a clean, dry surface.

After application of the solvents, the reservoir is dried with a hot air dryer or with an air or nitrogen line. Alternatively, the reservoir can be filled with solvent which is then vacuumed out, drying the reservoir in the process.

The disc and ball must be carefully cleaned prior to use, with particular care being taken to remove any protective surface coatings (such as anti-corrosive coatings) applied to prevent deterioration of the components prior to use. Cleaning can be effected using a soft tissue and then the disc and ball placed in separate beakers containing iso-octane or another suitable solvent. Each component is then cleaned in an ultrasonic cleaner for 2 minutes, the solvent then replaced with clean solvent, and cleaning resumed for another 10 minutes. The solvent is then replaced again and cleaning effected for a further 10 minutes, after which the components are dried with a clean, dry air line or with a nitrogen line.

The disc 11 and ball 12 are then mounted securely on their respective drive shafts.

Once the disc 11 and ball 12 have been secured in place, a number of tests can be conducted for a given lubricant under test. Each test will have a given temperature, normal load, speed and slide/roll ratio. These parameters may advantageously be stored in a computerised control system which cycles through the various tests, collecting and storing measurements from the force transducer 16 as it goes.

Figure 4:
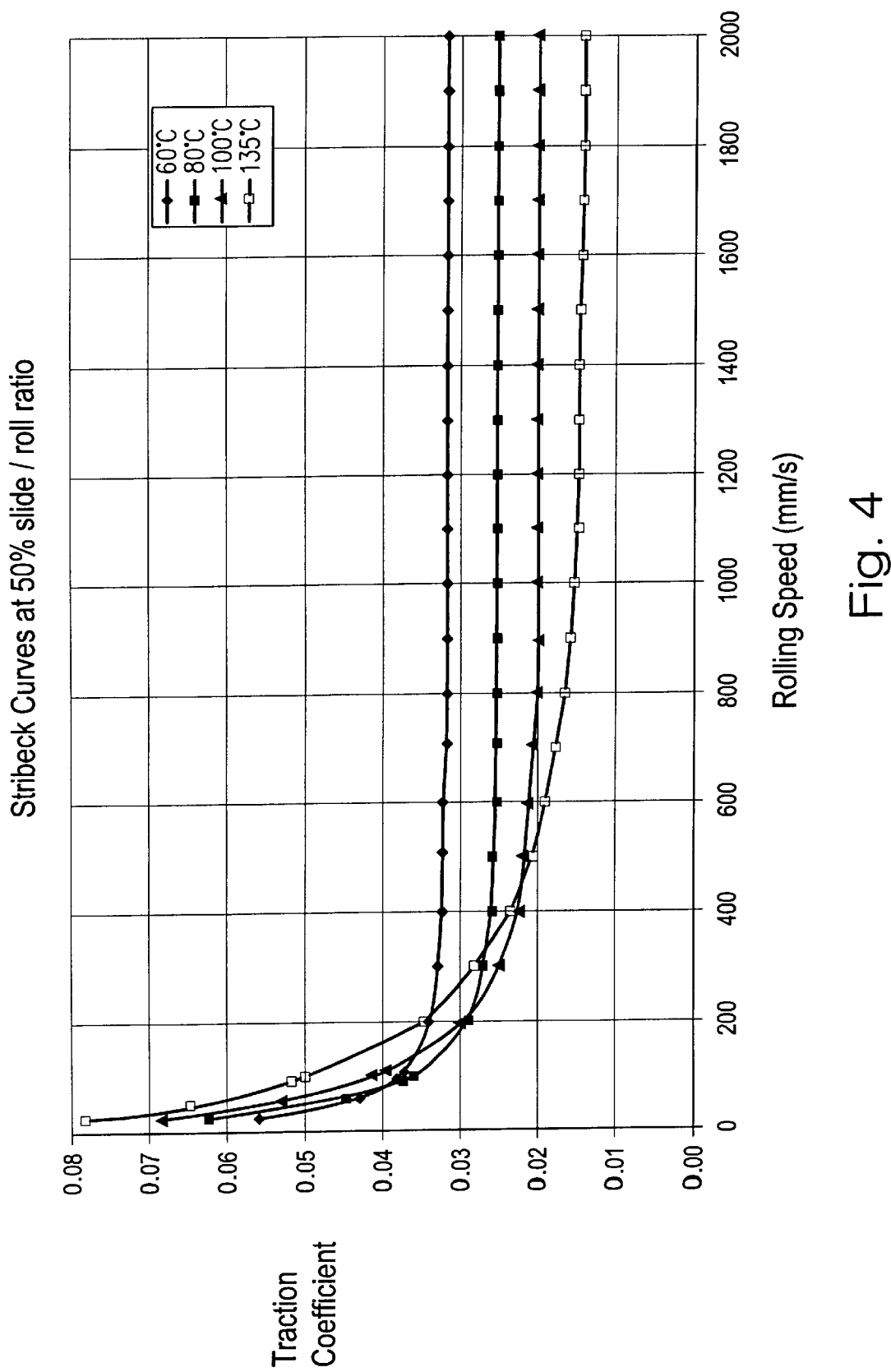
FIG. 4: shows various Stribeck Curves at 50% slide/roll ratio derived from use of the apparatus shown in FIGS. 1 to 3.
Figure 5:
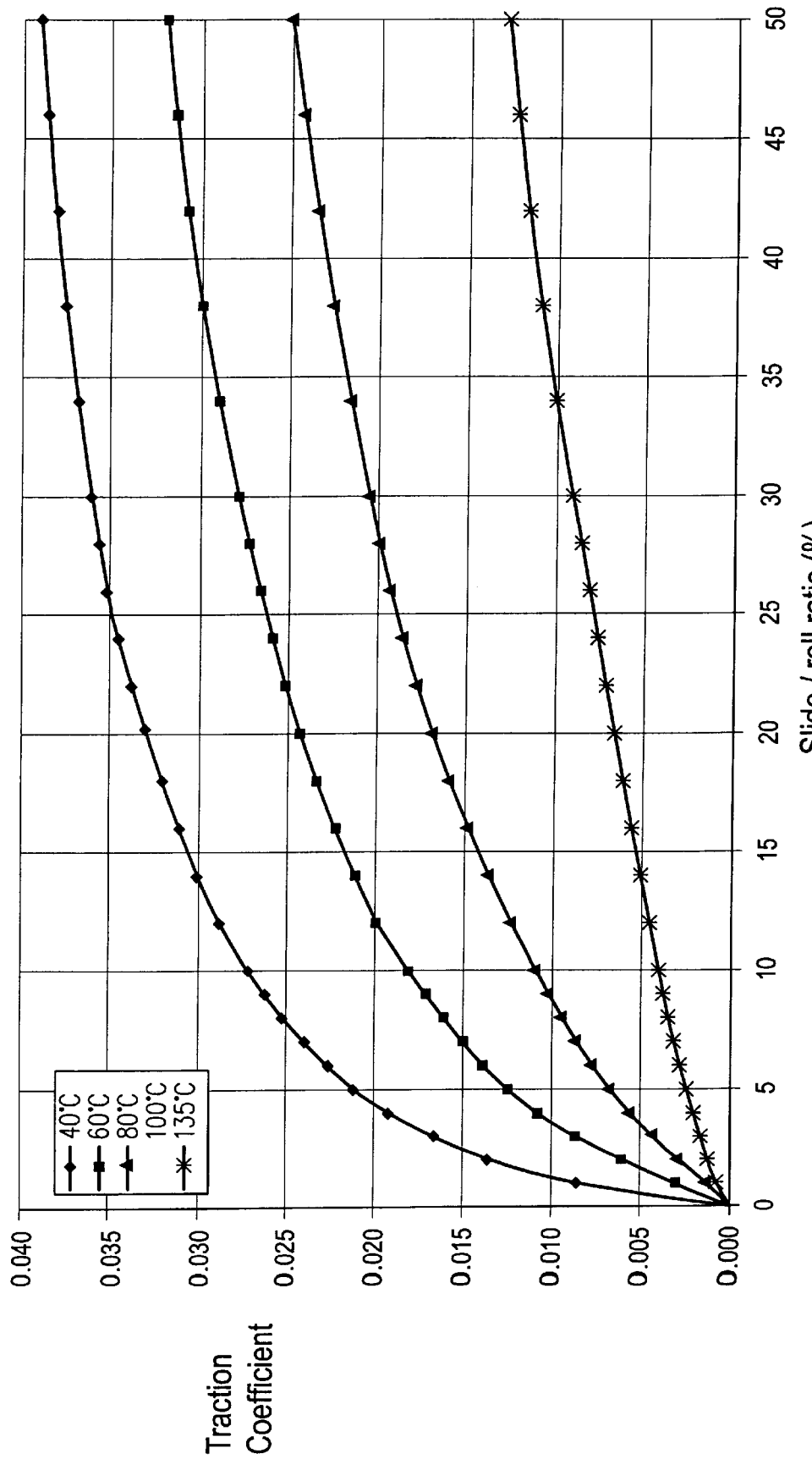
FIG. 5: shows plots of traction coefficient against slide/roll ratio at various different temperatures, derived from use of the apparatus shown in FIGS. 1 to 3.

Typical test output readings are shown in FIGS. 4 and 5.

It will thus be appreciated that the present invention provides a form of traction and/or friction testing apparatus which eliminates non-predictive forces from the test componentry, is compact in form and, at least in the preferred embodiment described, cycles through a variety of tests with the minimum of human intervention.

We claim:

1. A traction or friction testing apparatus, comprising:

a first traction surface;

a second traction surface constructed and arranged to, in use, contact said first traction surface, said first and second traction surfaces being arranged for rotational engagement therebetween;

a support structure constructed and arranged to support said first and second traction surfaces with respect to one another whilst allowing rotational movement therebetween;

drive means operable to effect differential rotation between said first and second traction surfaces and thereby to generate a traction or friction force therebetween; and force measuring means associated with at least one of said first and second traction surfaces to provide a measure arising from said traction or friction force, wherein the force arising between said first and second traction surfaces due to friction or traction therebetween is solely by elastic deformation of one or both of said support structure and said force measuring means;

wherein the support structure includes first support means arranged to rotatably mount said first traction surface and second support means arranged to rotatably support said second traction surface, said first and second support means being relatively displaceable to allow the first and second traction surfaces to be moved into contact with one another, with their respective axes of rotation lying in a substantially common plane;

wherein the second support means includes stiff elastic flexure means arranged to permit elastic movement of the second traction surface with respect to the first traction surface in the direction of a friction or traction force generated between said first and second traction surfaces, yet resist movement of the second traction surface in orthogonal directions; and wherein the force measuring means comprises a linear force transducer mounted to detect the force applied to the second traction surface due to traction or frictional engagement with said first traction surface, and is very much stiffer than said stiff elastic flexure means.

2. Apparatus as claimed in claim 1, wherein said first traction surface is planar in form whilst said second traction surface has a circular component to allow rotation thereof with respect to the first traction surface.

3. Apparatus as claimed in claim 1 wherein said second traction surface is provided by the surface of a spherical ball.

4. Apparatus as claimed in claim 1 wherein said first traction surface comprises a planar disc adapted to be mounted for rotation about its central axis.

5. Apparatus as claimed in claim 1 wherein, said first support means mounts said first traction surface for rotation about a substantially vertical axis and wherein said second support means is mounted for pivotal movement about a substantially horizontal axis to permit said second traction surface to be displaced into contact with said first traction surface.

6. Apparatus as claimed in claim 5 wherein said drive means includes displacement means to variably displace said second traction surface into contact with said first traction surface in a direction substantially normal to the plane of said first traction surface.

7. Apparatus as claimed in claim 6 wherein said displacement means is provided, in part, by a stepper motor.

8. Apparatus as claimed in claim 1 wherein said drive means includes a first drive motor to rotate said first traction surface, and a second drive motor to rotate said second traction surface.

9. Apparatus as claimed in claim 1 further including a reservoir constructed and arranged to retain a liquid immersion of the contact between said first and second traction surfaces.

10. Apparatus as claimed in claim 9 further including heating means associated with said reservoir to, in use, heat a liquid contained in said reservoir.

11. Apparatus as claimed in claim 9 further including cooling means asscoiated with said reservoir to, in use, cool a liquid contained in said reservoir.

12. Apparatus as claimed in claim 1, wherein said stiff elastic flexure means comprises a plurality of aluminum beams each shaped so as to have an elbow portion and arranged so that the elbow portion is adjacent to an elbow portion of at least one other of the aluminum beams.

\* \* \* \* \*